US012778959B2

(12) United States Patent
Bitto et al.

(10) Patent No.: US 12,778,959 B2
(45) Date of Patent: Nov. 3, 2026

(54) USE OF ISTRADEFILLIN TO REDUCE ORGAN FIBROSIS

(71) Applicant: SUNNUTRAPHARMA S.R.L., Messina (IT)

(72) Inventors: Alessandra Bitto, Messina (IT); Francesco Squadrito, Messina (IT); Domenica Altavilla, Messina (IT); Natasha Irrera, Messina (IT)

(73) Assignee: SunNutraPharma S.R.L., Messina (IT)

( * ) Notice: Subject to any disclaimer, the term of this patent is extended or adjusted under 35 U.S.C. 154(b) by 399 days.

(21) Appl. No.: 18/565,247

(22) PCT Filed: May 30, 2022

(86) PCT No.: PCT/IB2022/055053

§ 371 (c)(1),
(2) Date: Nov. 29, 2023

(87) PCT Pub. No.: WO2022/254311

PCT Pub. Date: Dec. 8, 2022

(65) Prior Publication Data

US 2024/0277718 A1 Aug. 22, 2024

(30) Foreign Application Priority Data

May 31, 2021 (IT) ........................ 102021000014177

(51) Int. Cl.

| | |
|---|---|
| ***A61K 31/522*** | (2006.01) |
| ***A61P 9/00*** | (2006.01) |
| ***A61P 11/00*** | (2006.01) |
| ***A61P 17/00*** | (2006.01) |

(52) U.S. Cl.

CPC ............. *A61K 31/522* (2013.01); *A61P 9/00* (2018.01); *A61P 11/00* (2018.01); *A61P 17/00* (2018.01)

(58) Field of Classification Search

CPC .......... A61K 31/522; A61P 9/00; A61P 17/00; A61P 11/00

See application file for complete search history.

(56) References Cited

FOREIGN PATENT DOCUMENTS

| | | | |
|---|---|---|---|
| EP | 3536343 | A1 | 9/2019 |
| WO | 2020000092 | A1 | 1/2020 |
| WO | 2020006631 | A1 | 1/2020 |

OTHER PUBLICATIONS

Tokano, Mieko, et al. "Istradefylline, an adenosine A2a receptor antagonist, ameliorates neutrophilic airway inflammation and psoriasis in mice." Clinical and Experimental Neuroimmunology 12.4 (2021): 268-275. (Year: 2021).*

Cronstein, B. N, "Adenosine receptors and fibrosis: a translational review", Faculty of 1000: Biol. Rpts., 3, Oct. 1, 2011.

Irrera, N. , et al., "PDRN, a Bioactive Natural Compound, Ameliorates Imiquimod-Induced rough NF-K[beta] Pathway Inhibition and Wnt/[beta]-Catenin Signaling Modulation", Int. J. Mol. Sci., 21(4), Feb. 12, 2020, 1215 (14 pgs).

Maher, T. M, et al., "Antifibrotic therapy for idiopathic pulmonary fibrosis: time to treat", Maher and Strek Resp. Res., 20(205), 2019, 9 pgs.

Park, S. , et al., "Cardiac fibrosis: potential therapeutic targets", Translational Res., 209, Jul. 1, 2019, 121-137.

Zhang, J. , et al., "Adenosine A2a Receptor Blockade Diminishes Wnt/[beta]-Catenin Signaling in a Murine Model of Bleomycin-Induced Dermal Fibrosis", Am. J. Pathol., 187(9), Sep. 1, 2017, 1935-1944.

* cited by examiner

*Primary Examiner* — Kamal A Saeed
*Assistant Examiner* — Quincy Mckoy
(74) *Attorney, Agent, or Firm* — Elmore Patent Law Group, P.C.; Joseph C. Zucchero; Carolyn S. Elmore

(57) ABSTRACT

The present invention concerns istradefylline use for the reduction of organ fibrosis.

10 Claims, 4 Drawing Sheets

USE OF ISTRADEFILLIN TO REDUCE ORGAN FIBROSIS

FIELD OF THE INVENTION

The present invention regards the use of istradefylline for the reduction of organ fibrosis.

STATE OF THE ART

Fibrosis is a process that involves different tissues of our body and fibrotic processes and it may be secondary to inflammation, such as in the case of autoimmune diseases or infectious one as in the case of COVID-19. Fibrosis outcomes may cause long-term sequelae on the quality of life and lifespan of patients. In fact, a fibrotic organ is characterized by limited regenerative functions and mostly functional limitations, that reduce the effectiveness of the actions performed, for example in the case of the lung, fibrosis limits the respiratory capacity of a subject who may also struggle in the performance of normal daily activities.

In this context, the Applicant has observed that there is a shortage of drugs which are effective in reducing fibrosis once it has established itself.

The Applicant therefore perceived that the identification of a new active ingredient capable of being effective in the treatment of fibrosis would therefore be desirable also considering the exponential increase in cases of organ fibrosis following the COVID-19 pandemic.

SUMMARY OF THE INVENTION

The purpose of the present invention is therefore to provide a new and more targeted approach to the treatment of organ fibrosis, and in particular of pulmonary, cardiac or skin fibrosis.

In accordance with the present invention, the Applicant has surprisingly found that it is possible to pursue the aforementioned object by using the active principle histradefylline.

Istradefylline (8-[(1E)-2-(3,4-Dimethoxyphenyl)ethenyl]-1,3-diethyl-3,7-dihydro-7-methyl-1H-purine-2,6-dione) is a compound with the following chemical structure:

(I)

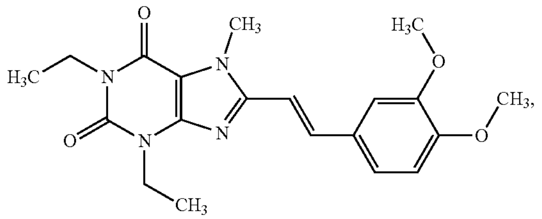

already known to be a selective A2A receptor antagonist and used for the treatment of Parkinson's disease.

The Applicant has surprisingly found that istradephylline acts on key points of the proliferation of connective tissue, thus succeeding in significantly reducing organ damage, with an improvement in the vital functions of the organs.

Therefore, the present invention relates in its first aspect to histradephylline for use in the treatment of pulmonary, cardiac or skin fibrosis.

DETAILED DESCRIPTION OF THE INVENTION

Figure 1:
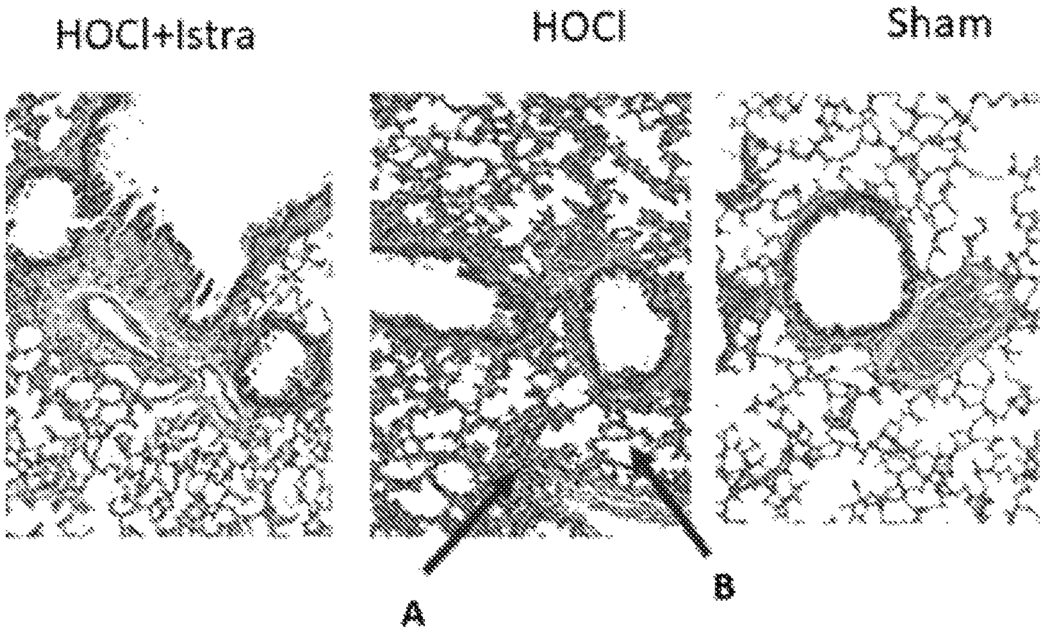
FIG. 1 shows the histological images of lung stained with Hematoxylin/Eosin of the animals subjected to the test according to the Example 1.

In the context of this description and in the subsequent claims, all numerical quantities indicating quantities, parameters, percentages, and so on are to be understood in all circumstances preceded by the term "about" unless otherwise indicated. Furthermore, all ranges of numerical quantities include all possible combinations of the maximum and minimum numerical values and all possible intermediate ranges, in addition to those specifically indicated below.

The present invention relates in a first aspect to histradephylline for use in the treatment of pulmonary, cardiac or skin fibrosis.

The Applicant has in fact surprisingly found that histradephylline acts on key points in the proliferation of connective tissue, thus managing to significantly reduce organ damage, with an improvement in the vital capacities of the organs themselves.

In particular, the Applicant has found that histradephylline is particularly suitable for the treatment of pulmonary, cardiac or skin fibrosis due to its ability to induce a reduction in the fibrotic damage induced by fibroblasts.

Therefore, in the treatment of fibrosis according to the present invention, an embodiment provides for the induction of a reduction of the fibrotic damage induced by fibroblasts by histradephylline.

This reduction of the fibrotic damage induced by fibroblasts is also advantageously performed by histradephylline through the modulation of the Wnt/b-catenin pathway.

Therefore, in the treatment of fibrosis according to the present invention which provides for a reduction of the fibrotic damage induced by fibroblasts, an embodiment provides for the modulation of the Wnt/b-catenin pathway by histradephylline.

Although the effectiveness of histradephylline in the treatment of organ fibrosis is not limited to a human subject, in one of its preferred embodiments, said treatment according to the invention is aimed at a human being, preferably suffering from an autoimmune disease.

In a preferred embodiment, the treatment of fibrosis according to the present invention with histradephylline is aimed at the treatment of pulmonary fibrosis, for example to a human being affected by COVID-19 or a chronic bronchopathy.

For the treatment according to the present invention, histradefylline can be administered by systemic administration including oral administration and parenteral administration.

In the context of the treatment according to the present invention, histradephylline can be administered once or according to a dosage regimen in which a certain number of doses are administered at variable time intervals for a given period of time. Dosage regimens suitable for histradephylline in the treatment according to the invention depend on the pharmacokinetic properties, such as absorption, distribution and half-life, which can be determined by the expert in the art. In addition, suitable dosage regimens, including the duration for which these regimens are administered, depend on the condition being treated, the severity of the condition being treated, the age and physical condition of the patient being treated, the medical history of the patient being treated, the nature of contemporary therapy, with the desired therapeutic effect, and similar factors which are within the knowledge and experience of the person skilled in the art.

Preferably, the treatment according to the present invention provides for the administration of histradefylline at a dosage ranging from 0.5 mg to 2 mg per day, per kilogram of body weight of the subject subjected to said treatment.

Histradephylline will normally, but not necessarily, be formulated in a pharmaceutical composition before administration to a patient. The pharmaceutical compositions of the invention are prepared using techniques and methods known to those skilled in the art.

The pharmaceutical compositions of the invention can be prepared and packaged in bulk form in which an effective amount of histradefylline is given to the patient as with powders, syrups and solutions for injection. Alternatively, the pharmaceutical compositions of the invention can be prepared and packaged in the form of unit dosages. A dose of the pharmaceutical composition according to the invention contains at least a therapeutically effective amount of histradephylline.

Preferably, the treatment of fibrosis according to the present invention is carried out with a composition comprising histradephylline and at least one pharmaceutically acceptable vehicle.

Preferably, said composition is administered to a subject who needs it orally.

Preferably said pharmaceutically acceptable vehicle is water or an aqueous vehicle (ie: saline solution, dextrose) and/or oily emulsions.

Histradephylline and any pharmaceutically acceptable excipient or excipients present will typically be formulated in a dosage form adapted for administration to the patient by the desired route of administration.

Conventional dosage forms include those adapted for (1) oral administration such as tablets, capsules, oval tablets, pills, lozenges, powders, syrups, elixirs, suspensions, solutions, emulsions, sachets and cachets; (2) parenteral administration as sterile solutions, suspensions and powders for reconstruction.

Pharmaceutically suitable excipients include the following types of excipients: diluents, fillers, binders, disintegrants, lubricants, granulating agents, glazing agents, wetting agents, suspending agents, emulsifiers, sweeteners, flavor masking agents, coloring agents, anti-agglomerants, humectants, plasticizers, viscosity enhancing agents, antioxidants, preservatives, stabilizers, surfactants and buffering agents. Suitable diluents and fillers include lactose, sucrose, dextrose, mannitol, sorbitol, starch, cellulose, calcium sulfate, and dibasic calcium phosphate. The oral solid dosage form may further comprise a binder. Suitable binders include starch, gelatin, sodium alginate, alginic acid, guar gum, povidone and cellulose and its derivatives (e.g. microcrystalline cellulose). The oral solid dosage form may further comprise a disintegrant. Suitable disintegrants include crospovidone, sodium starch glycolate, alginic acid and sodium carboxymethyl cellulose. The oral solid dosage form may further comprise a lubricant. Suitable lubricants include stearic acid, magnesium stearate, calcium stearate and talc. Suitable carriers for oral dosage form include, but are not limited to, magnesium carbonate, magnesium stearate, talc, lactose, pectin, dextrin, starch, methylcellulose, sodium carboxymethyl cellulose, and the like. The techniques used to prepare oral formulations are conventional mixing, granulating and squeezing or filling capsules.

Further features and advantages of the invention will be more evident from the following Examples, intended for illustrative and non-limiting purposes.

Experimental Section

Methods

Histological analysis, hematoxylin/eosin staining, Masson's trichrome and Picrosirius red: Tissues for histological and immunohistochemical analyses were fixed in 10% buffered formalin for 24 hours and then included according to standard paraffin protocol. The classic hematoxylin/eosin, Masson and Pricrosirius stainings were performed on 5-6 μm thickness tissue slices that were routinely processed using an automated histology preparer.

Immunofluorescence methods to mark vimentin and b-catenin: For immunohistochemistry the 5 μm tissue slices were incubated with 10 mmol/pH 6.0 citrate buffer in a temperature of 98° C. for 20 min. To reduce the background fluorescence, tissues were kept in a humidified chamber in 2 mmol/L glycine for 30 minutes. For the blocking of nonspecific antigenic sites, incubation was performed for 1 hour with 5% fetal bovine serum diluted in PBS, with the addition of 3% serum bovine albumin and 1% Triton X-100. Primary antibodies (p-Ser552 b-catenin, diluted 1:200; Cell Signal Technologies; Vimentin monoclonal antibody diluted 1:800; Sigma-Aldrich) were diluted in PBS and kept for 1 hour at room temperature. A species-specific antibody from Vector Laboratories was used as a negative control of the reaction. Secondary antibodies labeled with anti-rabbit IgG-fluorescein isothiocyanate (green fluorescence) or with anti-mouse IgG Alexa Fluor 555 (fred fluorescence) were kept for 1 hour at room temperature before mounting the slides and to observe the reaction under the microscope.

Total RNA extraction method: the extraction was performed with the Trizol reagent (Invitrogen) following the protocol suggested by the manufacturer without modifications.

Quantitative Real Time PCR Method: Reverse transcription was performed using the Super-Script IV Reverse Transcriptase synthesis kit (Thermo Fisher Scientific) and random primers as indicated in the manufacturer's protocol and 1 μl of cDNA was then used for the PCR reaction by using ready-made primers (to identify Wnt1, Wnt 5, Wnt 10, TGF-b, Collagen 1A1 and DKK1) and Thermo Fisher Scientific master mix in the QuantStudio 6 Flex instrument from Applied Biosystems.

Example 1

To demonstrate Istradefylline efficacy for the treatment of organ fibrosis laboratory animals, Balb/c mice, were used, and systemic fibrosis was induced with a solution of hypochlorous acid (HOCI), subcutaneously injected for 6 weeks. In fact, data obtained from literature indicate that it is possible to find a significant fibrosis in the major organs such as skin, heart, large vessels and lungs, already at the fourth week of induction of the disease: for this reason, the treatment with istradefylline started at the fourth week, carrying on both induction and treatment up to the sixth week.

Animals were divided into 3 groups of 7 animals each. A group was used as control group and was the group of untreated animals ("Sham"); a group was subcutaneously treated with 400 μl of an aqueous solution of hypochlorous acid (HOCI) for 6 weeks; lastly a group was subcutaneously treated with the above-mentioned solution of HOCI at the dose of 400 μl (for 6 weeks) and with istradefylline (from week 4 up to week 6) at the dose of 10 mg/kg per day intraperitoneally and 1 hour after HOCI injection ("HOCI+Istra").

At the end of the experiment, animals of all groups were killed and different organs were collected and skin, heart and lung sections to perform histological analysis (Hematoxylin/Eosin, Masson's trichrome and Picrosirius red) and immunofluorescence.

Figure 2:
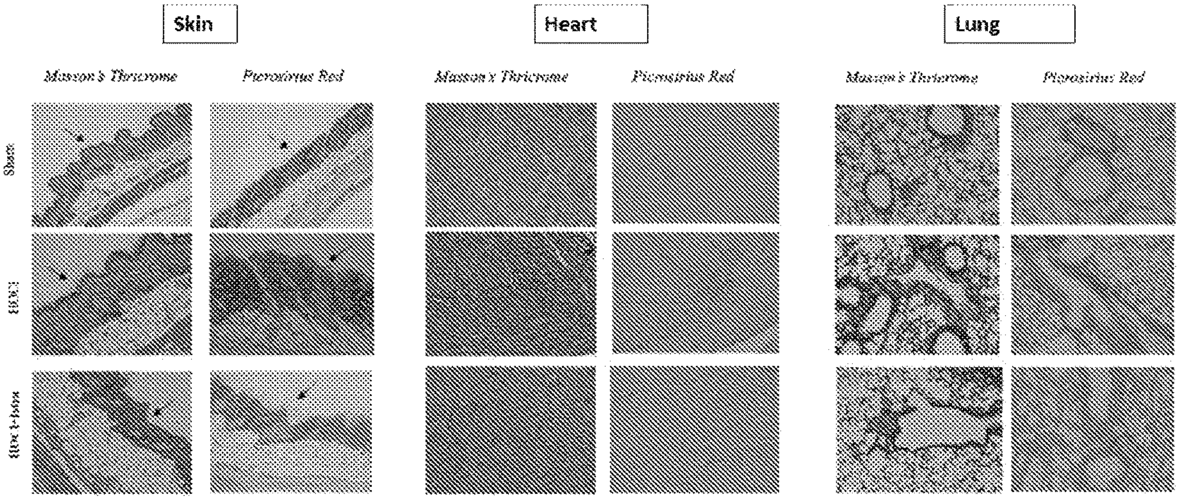
FIG. 2 shows the histological images of skin, heart and lung stained with Masson trichrome and Picrosirius red of the animals subjected to the test according to the Example 1.

From the analysis of the results obtained from histology with hematoxylin/eosin staining on the lung tissue samples (FIG. 1) it was possible to conclude that the administration of hypochlorous acid used to induce systemic sclerosis in the HOCI group, resulted in a significant increase of skin thickness as well as of myocardial and alveolar walls compared to the control group (Sham); on the other hand, istradefylline administration in the "HOCI+Istra" group showed that the active ingredient was able to significantly reduce the thickening both in skin and at the myocardial and pulmonary level compared to the HOCI group. The samples obtained from the animals of the HOCI and HOCI+Istra groups showed that this thickening could be caused by a significant accumulation of collagen fibers and in fact the excessive collagen deposition represents one of the main features of the fibrotic damage. In the tissues of the HOCI group it was also possible to observe phenomena of alveolar collapse (arrow "A" in FIG. 1), and destruction of the alveolar walls (arrow "B" in FIG. 1), also typical during COPD and COVID, which clearly indicates that the experimental model is adequate for studying new therapeutic approaches for this kind of diseases. Furthermore, the histological analysis following Masson trichrome and Picrosirius Red stainings (FIG. 2), both useful to highlight how the animals of the HOCI group, which developed fibrosis, showed a significant increase in collagen fibers deposition both in skin and in lung, especially around the pulmonary alveoli. In particular, as regards skin samples, in FIG. 2, collagen deposits are highlighted with arrows, respectively highlighted by Masson's trichrome and Picrosirius red stainings. However, as for heart and lung samples, the comparison of the images of the control group (Sham) and the HOCI and HOCI+Istra groups, allow us to appreciate the lower deposition of collagen fibers in the latter compared to the other groups, in particular to the HOCI group treated with hypochlorous which did not receive istradefylline.

It was also possible to observe how in the HOCI group at cardiac level the collagen deposits replaced the smooth muscle tissue typical of the heart, both on the right and on the left, also involving the deeper layers. Instead, istradefylline treatment (HOCI+Istra group) showed a significant reduction collagen fibers deposition compared to animals of the HOCI group, both in skin and in lung and heart tissues, thus demonstrating istradefylline efficacy in the treatment of parenchymal and fibrotic damage induced by excessive collagen deposition.

Figure 3:
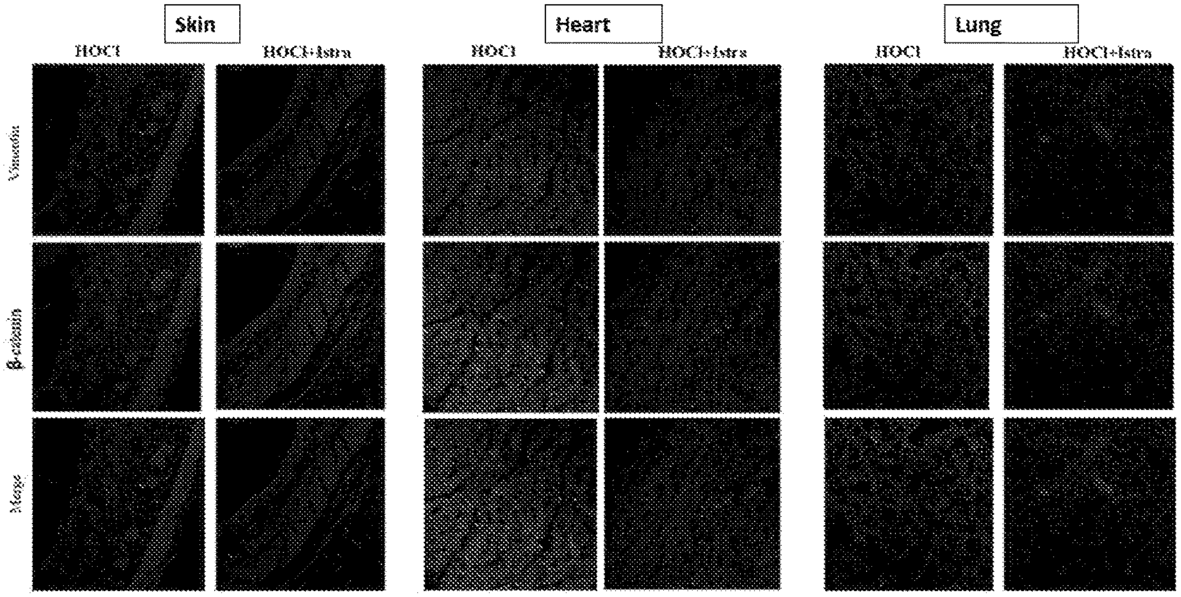
FIG. 3 shows the images of immunofluorescence reactions carried out on skin, heart and lung samples to highlight the presence of vimentin and beta-catenin of the animals subjected to the test according to the Example 1.

Finally, the results shown in FIG. 3, obtained by immunofluorescence to label vimentin ("Vimentin") and beta-catenin ("b-catenin"), as well as their overlap ("Merge"), highlighted how the animals of the HOCI group showed a widespread positivity for vimentin expression (therefore an increased number of fibroblasts) and for b-catenin (which demonstrates a proliferative activity of the labeled fibroblasts) both in skin, lung and heart, thus confirming that the established fibrotic damage is related to an increase of the fibroblastic component. In fact, vimentin is usually used as a marker of fibroblasts, a cell type particularly involved in fibrotic damage, and the activation of beta-catenin, which is an essential component of the Wnt/b-catenin pathway, may contribute to the fibrotic damage; moreover, beta-catenin activation may in turn induce the transcription not only of the genes involved in the fibrotic processes but also of the genes that encode for the same vimentin.

Furthermore, the results obtained allowed us to observe that the fibrotic process is also mediated by the Wnt/b-catenin pathway, as demonstrated by the co-localization of b-catenin in the labeled fibroblasts. As evident from FIG. 3, istradefylline administration (HOCI+Istra) significantly reduced the positivity of both b-catenin and vimentin in all studied tissues, confirming istradefylline efficacy in reducing the fibrotic damage induced by fibroblasts, through Wnt/b-catenin pathway modulation.

These data show that it was possible to significantly reduce fibrosis through istradefylline use and through a specific and new mechanism of action of this molecule.

To confirm the anti-fibrotic efficacy of istradefylline, especially in lungs, where the fibrotic process causes the impairment of respiratory function, the expression of the gene encoding Wnt1 was also studied. Indeed, the crosstalk between the Wnt/□-catenin pathway and the key mediator of fibrosis, the Transforming Growth Factor (TGF)-b, has been observed in previous experimental studies and it has been shown that the Wnt/b-catenin signaling up-regulates TGF-b, increasing its expression, and in turn TGF-b promotes b-catenin activation and stimulates collagen production.

Lungs obtained from the animals of all the experimental groups were subjected to the extraction of the total RNA which was then analyzed with the quantitative Real-Time PCR and specific primers to evaluate the expression of the genes encoding for TGF-b, Wnt1, Wnt5, Wnt10, DKK1 and Col1A1 (type I collagen) measured compared to the expression of the housekeeping gene, b-actin.

Figure 4:
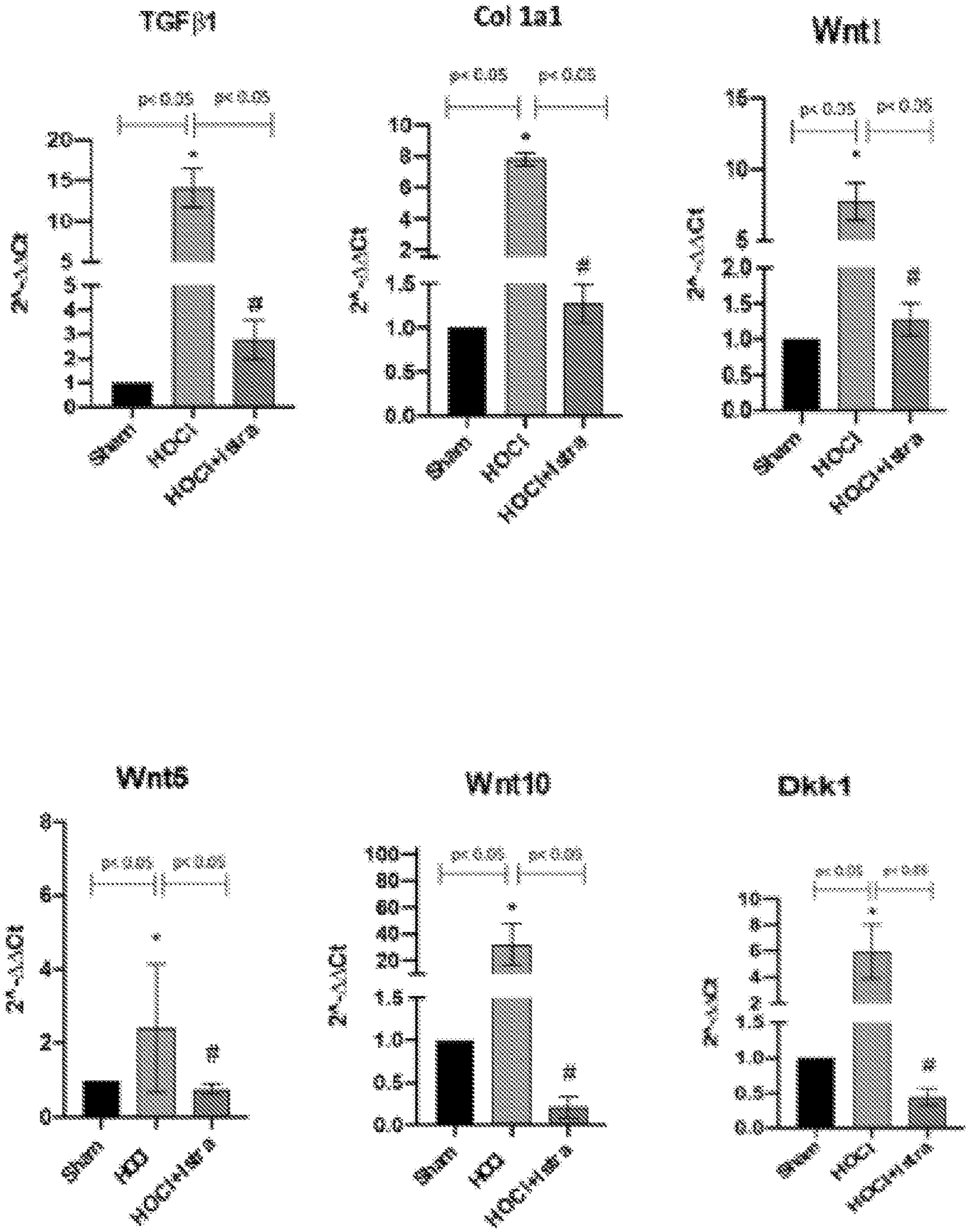
FIG. 4 shows the graphs with the results of the expression analysis of the genes encoding the Transforming Growth Factor beta, collagen and Wnt1 of the samples collected by the animals subjected to the test according to the Example 1 in the three groups: control group (Sham), fibrosis group (HOCl) and fibrosis group treated with histradefylline (HOCl+Istra).

Wnt1, 5, 10 and TGF-b were significantly increased in the animals that received HOCI only compared to the control group (Sham), whereas in the group of animals which received istradefylline from the fourth week (group HOCI+Istra) a significant reduction in the expression of all 3 targets was observed, demonstrating that istradefylline is able to inhibit the expression of genes closely related to the fibrotic process (FIG. 4). The statistical analysis showed a significance of 0.05 in the comparison between groups, confirming the validity of the performed tests.

The invention claimed is:

1. A method in the treatment of a pathology selected from the group consisting of lung fibrosis and heart fibrosis comprising the step of administering to a patient in need thereof istradefylline.

2. The method according to claim 1, wherein istradefylline induces a reduction in fibroblast-induced fibrotic damage.

3. The method according to claim 2, wherein istradefylline modulates Wnt/b-catenin pathway.

4. The method according to claim 1, wherein said treatment is aimed at a human being.

5. The method according to claim 4, wherein said human being is affected by a systemic sclerosis.

6. The method according to claim 1, wherein said treatment is a treatment for lung fibrosis.

7. The method according to claim 6, wherein said treatment is aimed at a human being affected by pulmonary fibrotic damage associated with a viral infection.

8. The method according to claim 6, wherein said treatment is aimed at a human being affected by pulmonary fibrotic damage associated with chronic obstructive pulmonary disease (COPD).

9. The method according to claim 1, wherein said treatment comprises the step of administering istradefylline at a dosage ranging from 0.5 mg to 2 mg per day, per kilogram of body weight of the human being subjected to said treatment.

10. The method according to claim 1, wherein said treatment is carried out with a composition comprising istradefylline and at least a pharmaceutically acceptable vehicle.

* * * * *